United States Patent
Haley et al.

(10) Patent No.: US 11,628,151 B2
(45) Date of Patent: *Apr. 18, 2023

(54) N,N-BIS-2-MERCAPTOETHYL ISOPHTHALAMIDE FOR THE TREATMENT OF NEURODEGENERATIVE DISEASES

(71) Applicant: EMERAMED LIMITED, Dublin (IE)

(72) Inventors: Boyd Eugene Haley, Nicholasville, KY (US); Ragnar Axel Theodor Klingberg, Stockholm (SE)

(73) Assignee: EMERAMED LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/953,622

(22) Filed: Sep. 27, 2022

(65) Prior Publication Data

US 2023/0013704 A1  Jan. 19, 2023

Related U.S. Application Data

(63) Continuation of application No. 17/558,975, filed on Dec. 22, 2021, which is a continuation of application No. 15/821,371, filed on Nov. 22, 2017, now abandoned, which is a continuation of application No. 15/313,877, filed as application No. PCT/GB2015/051572 on May 29, 2015, now abandoned.

(30) Foreign Application Priority Data

May 30, 2014 (GB) .................................... 1409662

(51) Int. Cl.
| | |
|---|---|
| A61K 31/166 | (2006.01) |
| A61P 25/28 | (2006.01) |
| A61K 45/06 | (2006.01) |
| A61K 31/428 | (2006.01) |
| A61K 31/13 | (2006.01) |
| A61K 31/198 | (2006.01) |
| A61K 31/4745 | (2006.01) |
| A61K 31/165 | (2006.01) |

(52) U.S. Cl.
CPC ............ *A61K 31/166* (2013.01); *A61K 31/13* (2013.01); *A61K 31/165* (2013.01); *A61K 31/198* (2013.01); *A61K 31/428* (2013.01); *A61K 31/4745* (2013.01); *A61K 45/06* (2013.01); *A61P 25/28* (2018.01); *Y02A 50/30* (2018.01)

(58) Field of Classification Search
CPC .............................. A61K 31/166; A61K 45/06
See application file for complete search history.

(56) References Cited

U.S. PATENT DOCUMENTS

| | | |
|---|---|---|
| 8,426,368 B2 | 4/2013 | Haley et al. |
| 2006/0099244 A1 | 5/2006 | Guilford |
| 2010/0227812 A1 | 9/2010 | Haley et al. |
| 2011/0237525 A1 | 9/2011 | Haley et al. |
| 2011/0237776 A1 | 9/2011 | Haley et al. |

FOREIGN PATENT DOCUMENTS

| | | |
|---|---|---|
| WO | 2011/038385 A2 | 3/2011 |
| WO | 2012/121798 A2 | 9/2012 |

OTHER PUBLICATIONS

Wenning et al., Lancet Neurol. Mar. 13, 2013; 12(3): 264-274.*
Declaration of Ragnar Klingberg Under 37 C.F.R. § 1.98 dated Dec. 6, 2018.
Hinz et al., "Amino Acid Management of Parkinson's Disease: A Case Study," International Journal of General Medicine 4:165-174 (2011).
Pocernich et al., "In-vivo Glutathione Elevation Protects Against Hydroxyl Free Radical-induced Protein Oxidation in Rat Brain," Neurochem Int 36(3):185-191 (2000).
Marcum et al., "Oxidation of Thiol-proteases in the Hippocampus of Alzheimer's Disease," Biochemical and Biophysical Research Communications 334(2):342-348 (2005).
Halliwell et al., "Chapter 9: Reactive Species and Disease: Fact, Fiction or Filibuster?" Free Radicals In Biology and Medicine (Fourth Edition), Oxford University Press 488-613 (Mar. 1, 2007).
Clarke et al., "Amelioration of Acute Mercury Toxicity by a Novel, Non-Toxic Lipid Soluble Chelator N,N'bis-(2-mercaptoethyl)isophthalamide: Effect on Animal Survival, Health, Mercury Excretion and Organ Accumulation," Toxicological and Environmental Chemistry 94(3):616-640 (2012).
PCT International Search Report and Written Opinion corresponding to PCT/GB2015/051572, dated Aug. 25, 2015.
Great Britain Search Report corresponding to GB1409662.2, dated Jan. 27, 2015.
Michele A. Faulkner "Safety Overview of FDA-Approved Medications for the Treatment of the Motor Symptoms of Parkinson's Disease," Expert Opinion on Drug Safety 13(8):1055-1069 (2014).

* cited by examiner

*Primary Examiner* — Alicia L Otton
(74) *Attorney, Agent, or Firm* — Troutman Pepper Hamilton Sanders LLP (Rochester)

(57) ABSTRACT

According to the invention there is provided N,N-bis-2-mercaptoethyl isophthalamide, or a pharmaceutically acceptable salt or derivative thereof, for use in the therapeutic treatment of a neurodegenerative disorder, such as Alzheimer's disease, Parkinson's disease, Huntington's disease and/or amyotrophic lateral sclerosis.

10 Claims, 4 Drawing Sheets

CTRL  +NBMI

N,N-BIS-2-MERCAPTOETHYL ISOPHTHALAMIDE FOR THE TREATMENT OF NEURODEGENERATIVE DISEASES

This application is a continuation of U.S. patent application Ser. No. 17/558,975, filed Dec. 22, 2021, which is continuation of U.S. patent application Ser. No. 15/821,371, filed Nov. 22, 2017 (now abandoned), which is a continuation of U.S. patent application Ser. No. 15/313,877 (now abandoned), which is a national stage application under 35 U.S.C. § 371 of PCT Application No. PCT/GB2015/051572, filed May 29, 2015, which claims the priority benefit of Great Britain Patent Application No. 1409662.2, filed May 30, 2014.

FIELD OF THE INVENTION

This invention relates to a new use of a known heavy metal-chelating compound.

Neurodegenerative Disorders

Neurological disorders are disorders of the body's nervous system, resulting in mental symptoms, such as confusion, altered levels of consciousness, and/or physical symptoms, including pain, loss of sensation, paralysis, muscle weakness, poor coordination and/or seizures.

All neurological disorders are characterised by one or more structural, biochemical and/or electrical abnormalities in the brain, spinal cord and/or other part of the nervous system.

The World Health Organization has estimated that neurological disorders and their sequelae affect as many as one billion people worldwide, and has also identified health inequalities and social stigma/discrimination as major factors contributing to the associated disability and suffering.

Amongst the many common neurological disorders, there is a sub-classification of "neurodegenerative" disorders (NDs), which includes Alzheimer's disease, Parkinson's disease, amyotrophic lateral sclerosis and Huntington's disease.

Neurodegenerative processes that lead to the latter conditions involve loss of structure and/or function (including death) of neurons, and may take place in many different levels of molecular and/or systemic neuronal circuitry.

Alzheimer's Disease

Alzheimer's disease (AD) is the most common form of dementia. There is presently no cure for AD, which is known to worsen as it progresses and eventually leads to death. AD is often diagnosed in the elderly, although early-onset of AD is not uncommon. In 2006, there were at least 26.6 million people worldwide affected by AD. With increased longevity, it has been predicted that it will affect 1 person in 85 people globally by 2050.

Early symptoms of AD include short-term memory loss. Once a patient is suspected to have the disease, diagnosis is typically confirmed by tests that evaluate behaviour, and/or a brain scan, with examination of brain tissue being required for a definitive diagnosis. The disease is thought to be associated with plaques and tangles in the brain (see, for example, Tiraboschi et al, *Neurology*, 62, 1984 (2004)).

Later symptoms include longer-term memory loss, confusion and irritability/aggression. Further decline results in inability to recognise family and friends. Eventually bodily functions are lost, with the end result typically being death. Life expectancy following diagnosis is approximately seven years, and fewer than 3% of individuals live more than 14 years after diagnosis.

One of the worst facets of AD is its degenerative nature, which means the sufferer becomes increasingly reliant on caregivers for assistance. This role is often filled by a spouse or a close relative, which usually places an enormous physical, psychological social and/or economic burden on such an individual. Thus, in addition to its primary healthcare treatment requirement, AD presents a significant burden on society.

Despite considerable research in the area over many years, including literally thousands of clinical trials, there is no known cure for AD, and available treatments offer relatively small symptomatic benefit and remain palliative in their nature. Currently-available medicines include acetylcholinesterase inhibitors (tacrine, rivastigmine, galantamine and donepezil), and the NMDA receptor antagonist, memantine. Nothing has been shown clearly to delay or halt the progression of AD and therefore its treatment represents a huge unmet clinical need.

Parkinson's Disease

Parkinson's disease (PD) is a ND of the central nervous system, which affects a sufferer's movement and coordination. The disease is fairly common (affecting approximately 0.15% of the population at any one time). Although it tends to be more prevalent in older people, it can also occur in younger adults.

The parts of the brain that are affected by the onset of PD include principally the substantia nigra, which is a part of the brain that controls motor function, as well as the nigrostriatal pathways and the locus coeruleus. The presence of the disease gives rise to reduced level of the key neurotransmitter, dopamine in these areas.

Reduced dopamine activity gives rise to numerous symptoms, many of them extremely unpleasant and embarrassing for the sufferer. The main symptoms are an uncontrollable tremor, particularly in the limbs, which is usually worse when a limb is at rest; increased rigidity/stiffness in the limbs ("cogwheeling"); and bradykinesias (reduced/slower movements, often manifest by shuffling when walking, soft speech and swallowing difficulties). However many other symptoms have been noted, including joint and muscle pain, dribbling, postural hypotension and dizziness, in addition to dementia, which can often occur at later stages of the disease.

Similar symptoms are also known to arise secondary to other causes including as a side-effect from certain antipsychotic and anti-nausea drugs and past encephalitis. Such secondary symptoms are usually referred to together as "parkinsonism".

There is no known cure for PD, although the symptoms can be alleviated (at least temporarily) by administration of levodopa, or "L-dopa". This drug works by increasing the levels of dopamine in the affected areas of the brain in order to control directly tremors and stiffness, and is still the best option for tackling the impaired motor symptoms.

L-dopa has its problems, however. Although initial treatment often results in alleviation of symptoms, long-term use gives rise to a notable variability in the drug's ability to control those symptoms (so-called "motor fluctuations"). Motor fluctuations may be manifest by end of dose deterioration (i.e. a sufferer noticing that the effect of his regular dose wears off prior to his scheduled time for the next dose), involuntary fidgety movements (dyskinesias) and, most disturbingly, sudden and unexpected re-appearance of symptoms, in particular stiffness.

As PD progresses, these motor fluctuations become more unpredictable. Thus, there remains a clear unmet clinical need for more effective treatments of PD.

Huntington's Disease

Huntington's disease (HD) is a genetic ND that affects muscle coordination and leads to cognitive decline and psychiatric problems. The disease is often manifest by abnormal involuntary writhing movements (chorea, hence the previous name "Huntington's chorea"). Physical symptoms of HD can start at any age, but usually begin between the ages of 35 and 44.

The disease is caused by an autosomal dominant mutation in either of an individual's two copies of the Huntingtin gene. Expansion of a CAG triplet repeat stretch within that gene results in a different (mutant) form of the Huntingtin protein that is expressed thereby, which gradually damages cells in the brain.

Early symptoms of HD are often minor changes in mood and/or cognition. This is often followed by increasing lack of coordination and mental decline, behavioural and psychiatric problems. Physical abilities are often impeded gradually until coordinated movement becomes very difficult. Mental abilities usually decline into dementia.

The various complications of HD reduce life expectancy to around twenty years from the point at which symptoms began.

There is no cure for HD, with full-time care often being required in the latter stages of the disease. Existing pharmaceutical treatments are only palliative. Treatment of HD therefore represents a huge unmet clinical need.

Amyotrophic Lateral Sclerosis

Amyotrophic lateral sclerosis (ALS), which is also known as motor neuron disease (MND), and sometimes Lou Gehrig's disease, is a ND characterised by rapidly progressive weakness due to muscular atrophy and spasticity, often resulting difficulty in speaking, swallowing and breathing.

Individuals affected by the disorder may ultimately lose the ability to initiate and control all voluntary movement. Sensory nerves and the autonomic nervous system are also generally unaffected, meaning the majority of patients maintain their sense of hearing, sight, touch, smell and taste.

Cognitive function is often unaffected in ALS sufferers, although if often coexists in individuals who also experience dementia, degenerative muscle disease, and degenerative bone disease as part of a syndrome called "multisystem proteinopathy".

Most people that contract ALS first experience it as "limb onset" ALS, and may thus experience difficulty or awkwardness when walking or running, manual dexterity (writing etc.). Fewer (about 25%) of cases comprise "bulbar onset" ALS, where patients first notice difficulty speaking clearly or swallowing and an even smaller proportion of patients experience "respiratory onset" ALS, with intercostal muscles being affected first.

The progression of ALS varies between patients, but eventually most patients are not able to use their limbs for anything, and/or lose the ability to speak and swallow food. Most end up on a portable ventilator. Difficulty in eating increases the risk of choking or aspirating food into the lungs. In later stages, maintaining a healthy weight can become a significant problem that may require the insertion of a feeding tube. Most people with ALS die of respiratory failure or pneumonia.

Treatments for ALS can presently only to relieve symptoms and moderately improve quality of life for patients, keeping them as mobile and comfortable as possible for as long as possible. Riluzole is the only treatment that has been found to improve survival, but only to a modest extent (see Ezekowitz et al, *American Family Physician*, 68, 2379 (2003)), and typically lengthens survival only by a matter of months. It is not capable of reversing the damage already done to motor neurons.

The provision of effective treatments of ALS therefore also represents a huge unmet clinical need.

Pathology of NDs

Intense research into the pathology and treatment of NDs has been conducted over many years. Some disorders are thought to be caused by genetic mutations; others are associated with the accumulation of intracellular toxic proteins (and are so classified as "proteinopathies").

Microglial cells are a type of resident immune that present in macrophages of the CNS system, including the brain and spinal cord. Microglia thus act as the main form of active immune defence in the CNS.

Microglia scavenge the CNS for plaques, damaged neurons and infectious agents. The brain and spinal cord are protected from the rest of the body by a series of endothelial cells (the blood-brain barrier). This barrier prevents most infections from reaching sensitive nervous tissue. Accordingly, microglial cells react quickly to decrease inflammation and destroy the infectious agents before they damage neural tissue.

There is a growing body of research that indicates that microglia may play a significant role in the pathogenesis of NDs. Chronic activation of microglia in NDs (including AD, PD, HD and ALS) results in release of a variety of pro-inflammatory substances (e.g. interleukin-1-beta (IL-1β), tumour necrosis factor alpha (TNF-α) and interleukin-1 (IL-6)) in the brain parenchyma, which is thought to contribute in a significant way to neurodegeneration (see, for example, Kaushik et al, *CNS Neurol. Disord. Drug Targets*, 12, 726 (2013), Kim et al, *Exp. Mol. Med.*, 38, 333 (2006), Wojtera et al, *Folia Neuropathol.*, 43, 311 (2005) and Khandelwal et al, *J. Neuroimmunol.*, 238, 1 (2011)).

Down-regulation of pro-inflammatory substances, such as TNF-α and IL-6 therefore represents a viable starting point for a potential treatment protocol for NDs generally.

In addition, AD is known to be caused by accumulation of abnormally folded beta-amyloid (Aβ) in the brain of affected individuals. This in turn stimulates a chronic inflammatory reaction, involving microglial activation, production of inflammatory cytokines and neurodegeneration (see, for example, Mazzitelli et al, *J. Neurosci.*, 31, 16969 (2011) and Joshi et al, Cell Death Differ., 21, 582 (2014)). It has also been shown that Aβ42 is phagocytised by activated microglia and released back as a form susceptible of differential aggregation, increasing plaque formation and neuronal death.

Although the relationship between neuroinflammation, AR formation and deposition, and neuronal death is still unclear, preventing soluble AR formation represents a major goal in the treatment of AD.

DISCLOSURE OF THE INVENTION

N,N-bis-2-mercaptoethyl isophthalamide (NBMI) was first disclosed in U.S. Pat. No. 6,586,600 B2. Its use as a dietary supplement, and in the relief of oxidative stress is disclosed in US patent application 2010/0227812. NBMI is known to be a powerful chelator of heavy metals, including mercury, cadmium and lead. See also Patel et al, *Toxicology Mechanisms and Methods*, 22, 383 (2012).

Analogues of NBMI have been disclosed in inter alia U.S. Pat. No. 8,426,368 B2 and international patent applications WO 2011/038385 and WO 2012/121798. However, none of these documents disclose the potential use of NBMI or related compounds in the potential treatment of NDs, such as AD, PD, HD or ALS.

We have found not only that NBMI is surprisingly capable of inhibiting release of key anti-inflammatory markers, such IL-6, that are known to be expressed in patients with NDs, such as AD, PD, HD and ALS (see, for example, Urrutia et al, Front Pharmacol., 10, 38 (2014)), but also, even more surprisingly, that NBMI may be capable of modifying the aggregation state of Aβ42 and microglia activation, by reducing TNF-α production and increasing Aβ42-488 release, so reducing neuronal death.

We therefore believe that NBMI may be administered to patients to treat NDs therapeutically by ameliorating symptoms and modifying/abrogating the progression of such diseases, without giving rise to significant adverse side effects.

According to a first aspect of the invention there is provided NBMI, or a pharmaceutically-acceptable salt thereof or derivative thereof, packaged and presented for use in a method of treating a ND. Such a method comprises administering a pharmaceutically-effective amount of NBMI, or a pharmaceutically-acceptable salt thereof, or a pharmaceutically-acceptable derivative thereof, to a patient in need of such treatment.

The term "ND" will be understood to include any disorder, disease or condition characterised for example by neurodegenerative processes that involve loss of structure and/or function (including death) of neurons, and/or any degenerative condition characterised by accumulation and/or aggregation of (e.g. intracellular toxic) proteins (i.e. "proteinopathies"), such as ALS (including multisystem proteinopathy), AD, PD and prion diseases, such as Creutzfeldt-Jakob disease (and other transmissible spongiform encephalopathies), as well as HD.

Also included under the ND definition herein are rarer conditions, referred to in the literature variously as ataxia telangiectasia, autosomal dominant cerebellar ataxia, Batten disease (including Spielmeyer-Vogt-Sjögren-Batten disease), Corticobasal degeneration (including Corticobasal ganglionic degeneration), fatal familial insomnia, hereditary motor and sensory neuropathy with proximal dominance, infantile Refsum disease, locomotor ataxia, Lyme disease, Machado-Joseph disease (also known as Machado-Joseph Azorean disease, Joseph's disease, spinocerebellar ataxia type 3 (SCA3) mental retardation, microcephaly with pontine and cerebellar hypoplasia (also known as mental retardation, X-linked, syndromic, Najm type), multiple system atrophy (including Shy-Drager syndrome), neuroacanthocytosis, pontocerebellar hypoplasia, pyruvate dehydrogenase deficiency (also known as pyruvate dehydrogenase complex deficiency), Refsum disease, Sandhoff disease (including Sandhoff-Jatzkewitz disease, variant 0 of GM2-gangliosidosis or hexosaminidase A and B deficiency), spinocerebellar ataxia, subacute combined degeneration of spinal cord (Lichtheim's disease), subacute sclerosing panencephalitis, tabes *dorsalis* (also known as syphilitic myelopathy), Tay-Sachs disease (also known as GM2 gangliosidosis or hexosaminidase A deficiency), toxic encephalopathy and toxic leukoencephalopathy.

Conditions that may be mentioned more specifically include AD, PD (including Parkinsonism), HD (including Huntington's chorea) and all conditions various associated with ALS (including Lou Gehrig's disease, and all other forms of motor neuron disease, such as primary lateral sclerosis, progressive muscular atrophy, progressive bulbar palsy and pseudobulbar palsy).

For the avoidance of doubt, in the context of the present invention, the terms "treatment", "therapy" and "therapy method" include the therapeutic, or palliative, treatment of patients in need of, a ND, or other relevant conditions mentioned herein. "Patients" include human patients.

Pharmaceutically-acceptable salts of NBMI that may be mentioned include alkaline earth, and more particularly alkali, metal salts, such as lithium, sodium, potassium, rubidium, caesium and francium salts.

Such salts may be formed by conventional means, for example by reaction of NBMI with one or more equivalents of an appropriate base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of an active ingredient in the form of a salt with another counter-ion, for example using a suitable ion exchange resin.

Pharmaceutically-acceptable derivatives of NBMI include glutathione derivatives, cysteine derivatives, alpha-dihydrolipoic acid derivatives, cystamine derivatives, thiolphosphate derivatives, 5'-thioladenosine derivatives, L-homocysteine, co-enzyme A derivatives, 2-mercaptoethanol derivatives, dithiothreitol derivatives, iodoacetate derivatives, bromoacetate derivatives, fluoroacetate derivatives, or chloroacetate derivatives, of NMBI. Such derivatives may be prepared as described in, for example, US patent application 2011/0237776.

According to a further aspect of the invention there is provided a method of treating a ND in a patient by (packaging, presenting and/or) administering NBMI, or a pharmaceutically-acceptable salt or derivative thereof, at a sufficient, pharmaceutically-effective dose.

NBMI may be of use in the relief of symptoms of NDs, including those mentioned hereinbefore for the various conditions.

According to a further aspect of the invention there is provided a method of relieving one or more symptom of a ND in a patient suffering from that ND, which method comprises administering NBMI, or a pharmaceutically-acceptable salt or derivative thereof, to such a patient.

In the uses and methods described herein, NBMI is preferably administered locally or systemically, for example orally, intravenously or intraarterially (including by intravascular or other perivascular devices/dosage forms (e.g. stents)), intramuscularly, cutaneously, subcutaneously, transmucosally (e.g. sublingually or buccally), rectally, transdermally, nasally, pulmonarily (e.g. by inhalation, tracheally or bronchially), topically, or by any other parenteral route, in the form of a pharmaceutical preparation comprising the compound in a pharmaceutically acceptable dosage form. Preferred modes of delivery include oral (particularly), intravenous, cutaneous or subcutaneous, nasal, intramuscular, or intraperitoneal delivery.

In packaging and presenting it for use in the treatment of a ND disorder, NBMI will generally be administered in the form of one or more pharmaceutical formulations in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Such pharmaceutically acceptable carriers may also impart an immediate, or a modified, release of NBMI.

Suitable pharmaceutical formulations may be commercially available or otherwise are described in the literature, for example, Remington *The Science and Practice of Pharmacy*, 19th ed., Mack Printing Company, Easton, Pa. (1995) and *Martindale—The Complete Drug Reference* (35$^{th}$ Edition) and the documents referred to therein, the relevant disclosures in all of which documents are hereby incorporated by reference. Otherwise, the preparation of suitable formulations may be achieved non-inventively by the skilled person using routine techniques. Suitable pharmaceutical formulations for use with NBMI are also described in US patent application 2010/0227812.

The amount of NBMI/salt/derivative in the formulation will depend on the severity of the condition, and on the patient, to be treated, as well as the compound(s) which is/are employed, but may be determined non-inventively by the skilled person.

Depending on the patient to be treated, as well as the route of administration, NBMI may be administered at varying therapeutically effective doses to a patient in need thereof.

However, the dose administered to a human, in the context of the present invention should be sufficient to effect a therapeutic response over a reasonable timeframe (as described hereinbefore). One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the age, condition, body weight, sex and response of the patient to be treated, and the stage/severity of the disease, as well as genetic differences between patients.

Administration of NBMI may be continuous or intermittent (e.g. by bolus injection). The dosage may also be determined by the timing and frequency of administration.

Suitable doses of NBMI are therefore in the range of about 0.05 and about 100.0 mg, including between about 0.1 (e.g. about 1) and about 50 (e.g. about 60) mg, for example between about 0.5 (e.g. about 1.5) and about 10 (e.g. about 40) mg of the compound per kilogram of the patient's total body weight per day.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

In the uses and methods described herein, NBMI may also be combined with one or more active ingredients that are potentially useful, or have been indicated for use, in the treatment of a ND. Such patients may thus also (and/or already) be receiving therapy based upon administration of one or more of such active ingredients, by which we mean receiving a prescribed dose of one or more of those active ingredients mentioned herein, prior to, in addition to, and/or following, treatment with NBMI.

Such active ingredients include, for example, for AD, cholinesterase inhibitors, such as donepezil, rivastigmine, tacrine and galantamine, and NMDA receptor antagonists, such as memantine; for PD, L-dopa (and optionally dopamine decarboxylase inhibitors, such as carbidopa or benserazide (which may be given in combination with L-dopa)), dopamine agonists (including bromocriptine, pergolide, pramipexole, ropinirole, pribedil, cabergoline, apomorphine, lisuride and rotigotine), MAO-B inhibitors (such as selegline and rasagiline), or other PD drugs (such as amantadine and anticholinergics); for HD, tetrabenazine and other drugs that help to reduce chorea include neuroleptics and benzodiazepines), amantadine or remacemide; and for ALS, riluzole, as well as baclofen and diazepam (often prescribed to control spasticity caused by ALS) and trihexyphenidyl and amitriptyline (often prescribed when ALS patients begin having trouble swallowing saliva), as well as other drugs that may be used in the treatment of NDs.

Pharmaceutically-acceptable salts of other active ingredients useful in the treatment a ND that may be mentioned include acid addition salts and base addition salts. Such salts may be formed by conventional means. Such compounds and salts are referred to hereinafter together as "ND compound(s)".

Suitable doses of such ND compounds are known to those skilled in the art and include those listed for the drugs in question to in the medical literature, such as *Martindale—The Complete Drug Reference* (35$^{th}$ Edition) and the documents referred to therein, the relevant disclosures in all of which documents are hereby incorporated by reference.

This aspect of the invention provides for the administration of NBMI in conjunction with an ND compound, as hereinbefore defined. Such combinations may thus be presented either as separate formulations, wherein at least one of those formulations comprises NBMI or salt/derivative thereof, and at least one comprises the ND compound, or may be presented (i.e. formulated) as a combined preparation (i.e. presented as a single formulation including NBMI/salt/derivative and a ND compound).

Thus, there is further provided:

(1) a pharmaceutical formulation including NBMI, or a pharmaceutically-acceptable salt or derivative thereof; one or more ND compound; and a pharmaceutically-acceptable adjuvant, diluent or carrier (which formulation is hereinafter referred to as a "combined preparation"); and (2) a kit of parts comprising components:
(A) a pharmaceutical formulation including NBMI, or a pharmaceutically-acceptable salt or derivative thereof, in admixture with a pharmaceutically-acceptable adjuvant, diluent or carrier; and
(B) a pharmaceutical formulation including one or more ND compound, in admixture with a pharmaceutically-acceptable adjuvant, diluent or carrier,
which components (A) and (B) are each provided in a form that is suitable for administration in conjunction with the other.

According to a further aspect of the invention, there is provided a method of making a kit of parts as defined above, which method comprises bringing component (A), as defined above, into association with a component (B), as defined above, thus rendering the two components suitable for administration in conjunction with each other.

By bringing the two components "into association with" each other, we include that components (A) and (B) of the kit of parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

Thus, there is further provided a kit of parts comprising:
(I) one of components (A) and (B) as defined herein; together with
(II) instructions to use that component in conjunction with the other of the two components.

The kits of parts described herein may comprise more than one formulation including an appropriate quantity/dose of NBMI/salt/derivative, and/or more than one formulation including an appropriate quantity/dose of ND compound, in order to provide for repeat dosing. If more than one formulation (comprising either active compound) is present, such formulations may be the same, or may be different in terms of the dose of either compound, chemical composition(s) and/or physical form(s).

NMBI/salt/derivative may also be co-administered with antioxidants or chelators, including vitamin-E, vitamin-D, cysteine, cystine, glutathione, lipoic acid glutathione (GSH), dihydrolipoic acid (DLPA), lipoic acid (LPA), N-acetylcysteine (NAC), dimercaptopropane sulfonate (DMPS), dimercaptosuccinic acid (DMSA), ethylenediaminetetraacetic acid (EDTA), and mixtures thereof.

Wherever the word "about" is employed herein, for example in the context of amounts (e.g. doses of active ingredients), it will be appreciated that such variables are approximate and as such may vary by ±10%, for example ±5% and preferably ±2% (e.g. ±1%) from the numbers specified herein.

The uses/methods described herein may have the advantage that, in the treatment of relevant NDs, they may be more convenient for the physician and/or patient than, be more efficacious than, be less toxic than, have a broader range of activity than, be more potent than, produce fewer side effects than, or that it may have other useful pharmacological properties over, similar methods (treatments) known in the prior art for use in therapy of the relevant ND.

The invention is illustrated, but in no way limited, by the following example, in which.

Example 1

Figure 1:
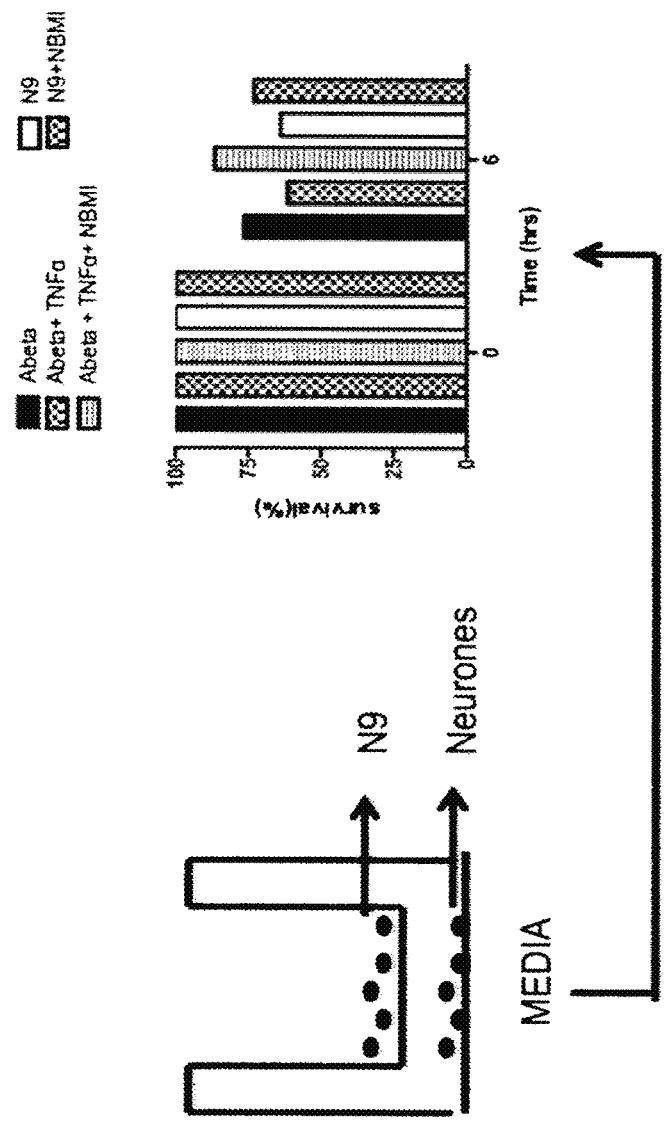
FIG. 1 illustrates the effect of NBMI Aβ42-induced cell death in primary neurons incubated with oligomeric Aβ42 and co-cultured in with N9 cells.

Inhibition of IL-6 and IL-8 Using NBMI

Secretion of the pro-inflammatory cytokines interleukin (IL)-6, IL-8 (as well as GM-CSF and MCP-1) into cell media in response to particle exposure was measured in A549 and BEAS-2B cells using the following method.

Lung epithelial cells were seeded at $5 \times 10^4$ in 24-well plates. After pre-incubation with NBMI, the antioxidant compound, N-acetyl-L-cysteine (NAC), which was used as a positive control, or vehicle, for 3 hours the medium was removed.

Fresh media containing various particles (as below) in different concentrations was in a total volume of 0.5 ml for an additional 24 hours. The supernatants were then separated from the cells by centrifugation.

IL-8, IL-6, GM-CSF and MCP-1 were measured in the cell free fluid using the DuoSet ELISA Development kit (R&D Systems, Abingdon, UK) according to manufacturer's protocol.

Exposure to medium only served as negative control. Each experiment was performed twice with 4 replicates.

In general, both titanium dioxide type P25 and urban dust (reference SRM 1649 b) induced production of pro-inflammatory cytokines in the lung epithelial cell lines A549 and BEAS-2B.

The effect of pre-incubation with 50 µM NBMI on particle-induced cytokine formation was tested at various concentrations of particles.

The study demonstrated that NBMI can reduce the particle-induced secretion of pro-inflammatory cytokines in both cell lines, although the reduction was only in some cases reduced to background levels.

The highest concentrations of IL-8 and IL-6 were achieved in supernatants of A549 cells exposed to $TiO_2$ P25 at 75 µg/cm². At this dose, 50 µM NBMI reduced the secretion of IL-8 with 29% and IL-6 with 38%.

At 100 µg/cm² of Urban Dust in A549 cells, pre-incubation with 50 µM NBMI reduced the secretion of IL-8 with 30%, and IL-6 with 38%.

At 100 µg/cm² of $TiO_2$ P25 in BEAS-2B cells, pre-incubation with 50 µM NBMI reduced the secretion of IL-8 with 49%, and IL-6 with 37%.

At 100 µg/cm² of Urban Dust in BEAS-2B cells, pre-incubation with 50 µM NBMI reduced the secretion of IL-6 with 47%.

Pre-incubation with 5 mM NAC was also effective in reducing the secretion of inflammatory cytokines.

Example 2

Modulation of Microglia Activation Following Aβ42 Administration Using NBMI

Aβ42 stock was solubilized in DMSO at a concentration of 2 mM, vortexed and sonicated for 2 minutes to ensure complete dissolution. Aβ42 was diluted in 50 mM NaPi, 100 mM NaCl (pH 7.4) buffer at a concentration of 200 µM and was used within 3 hours at a final concentration of 200 nM.

Primary cultures of cortical neurons were prepared from the cerebral cortex of mice at embryonic stage 17 (E17). The cells from each cortex were seeded separately on poly-L-ornithine (Sigma) pre-coated 6-well plates at a density of $0.25 \times 10^6$ cells/cm² in Neurobasal media containing B27 supplement with antioxidant, 1% penstrep and 1% glutamine.

After 10 days' incubation, neurons were used in experiments. Where indicated, cells were pre-treated for 30 minutes with NBMI (10 nM) added directly to the cell culture medium.

To determine cell viability, cells were washed with PBS (pH 7.4). MTT solution (3-(4,5-dimethylthiazol-2yl)-2,5-diphenyl tetrazolium bromide) was added to cells for 30 minutes at 37° C. After three washes, the insoluble formazan product was dissolved in dimethyl sulfoxide. The optical density of each culture well was then measured using a micro-plate reader (Molecular Probes, Garching, Germany) at 550 nm. The optical density of formazan formed in control cells was taken as 100% of viability.

N9 cells were maintained at 37° C. and 5% $CO_2$ in RPMI 1640 (Gibco Laboratories, USA), supplemented with 10% heat-inactivated fetal bovine serum (FBS) and 0.5% penicillin-streptomycin.

TNF-α secretion from primary microglia and the BV2 cell line was valued by a specific sandwich-type enzyme-linked immunoabsorbent assay (ELISA) (Duoset, R&D system) according to the manufacturer's instructions. Intracellular concentration of Aβ42 was measured using a specific sandwich-type ELISA assay (human Aβ42 kit, Invitrogen, KHB3441 and mouse/rat, IBL 27721; Immuno-Biological Laboratories Co., Ltd., Japan) according to the manufacturer's instructions.

Homogenization was performed with a cold 4× volume of PBS supplemented with the 1× protease inhibitor cocktail, followed by the addition of a solution 8.2 M guanidine/82 mM Tris HCl (pH 8.0) to yield a solution with a 5M final guanidine concentration.

N9 cells were treated with 200 nM Aβ42488 (Anaspect), and AR internalization was recorded in culture for 24 hours after AR administration using a CellIR microscope, with the image processed using CellIR software.

Results

NBMI reduced Aβ42-induced cell death in primary neurons incubated with oligomeric Aβ42 and co-cultured in with N9 cells (see FIG. 1).

Figure 2A:
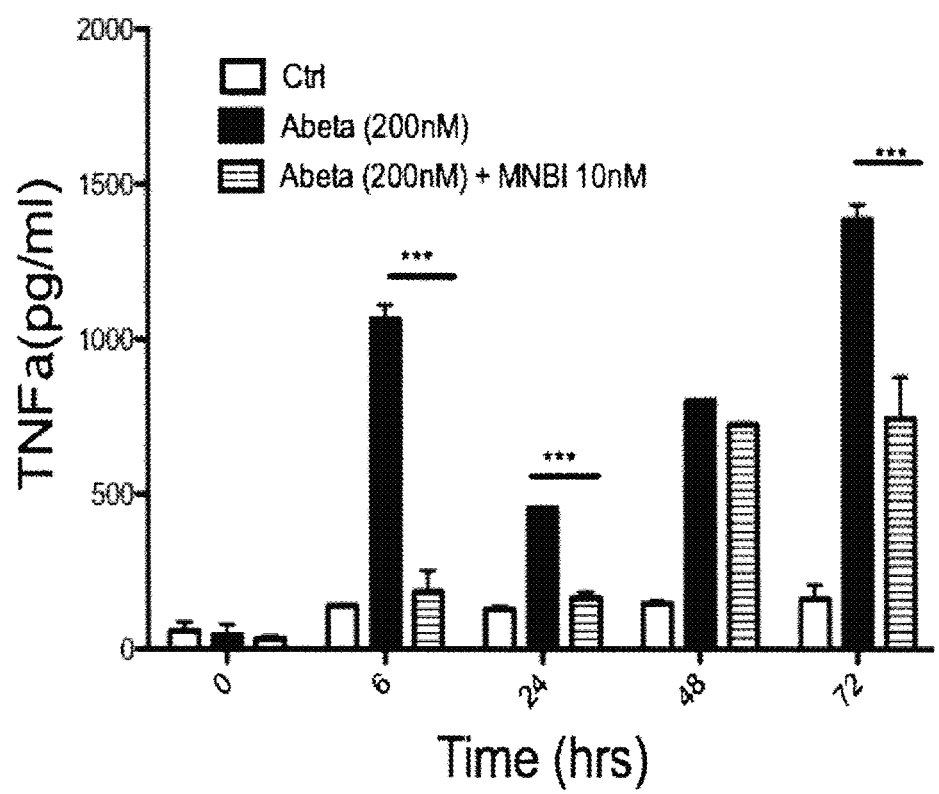
FIG. 2A illustrates the effect of NBMI on primary microglia activation (evaluated as TNF-α release) following Aβ42 administration.
Figure 2B:
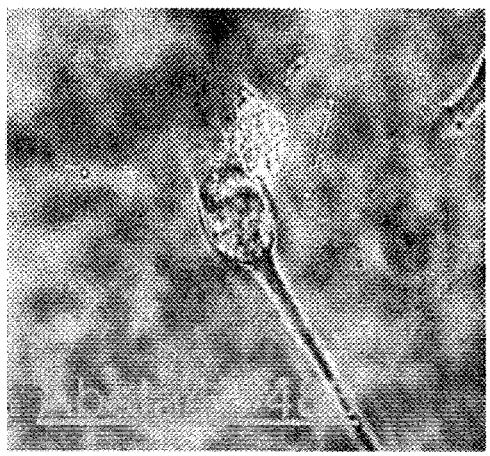
FIG. 2B illustrates the effect of NBMI on modulated internalization of Aβ42 by microglia following Aβ42 administration.
Figure 2B:
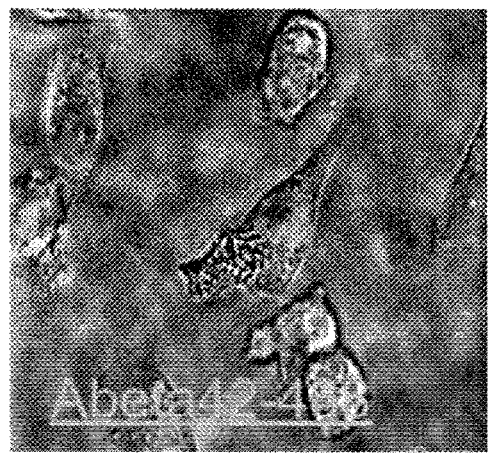

NBMI also blocked primary microglia activation (evaluated as TNF-α release) following Aβ42 administration (see FIG. 2A) and modulated internalization of Aβ42 by microglia (FIG. 2B).

Figure 3:
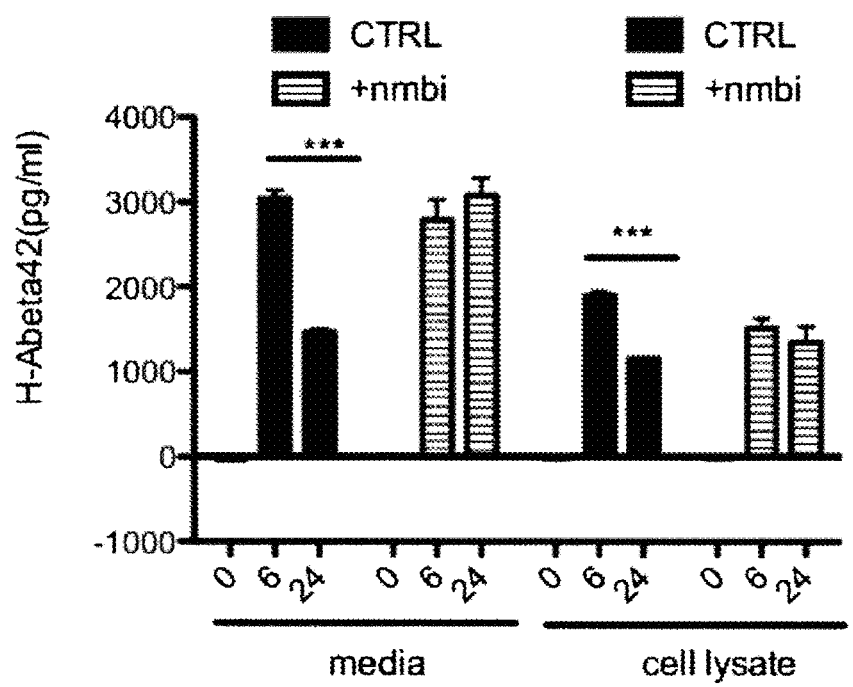
FIG. 3 illustrates the effect of NBMI on the aggregation state of Aβ42 in media and in the cell lysate cultures following its administration in primary microglia cultures.

NBMI changed the aggregation state of Aβ42, both in the media and in the cell lysate cultures following its administration in primary microglia cultures (FIG. 3).

These results indicate the ability of NBMI to affect microglia activation, the aggregation state of Aβ42 and Aβ42 neurotoxicity. The decrease in the detection of the Aβ42 c-ter fragment by ELISA (FIG. 3) strongly suggests a change in the conformation state of Aβ42, which prevents the interaction between the c-ter-directed antibody and Aβ42 in the media.

NBMI's ability to restore neuronal survival in hippocampal neurons co-cultured with N9 cells and incubated with Aβ42; block microglia activation and TNF-α production in response to Aβ42; and modify Aβ42 aggregation, and therefore its interaction with microglia cells means that it is potentially of use in preventing neuronal death and this in the treatment of AD.

The invention claimed is:

1. A method of treatment of multiple system atrophy, which method comprises:
administering N,N-bis-2-mercaptoethyl isophthalamide, or a pharmaceutically acceptable salt thereof, to a patient having multiple system atrophy (MSA) in a manner effective to treat the MSA.

2. The method of claim 1, wherein N,N-bis-2-mercaptoethyl isophthalamide or salt thereof is administered to the patient in an amount between about 1.5 mg and about 10.0 mg per kilogram of the patient's total body weight per day.

3. The method of claim 1, wherein N,N-bis-2-mercaptoethyl isophthalamide is administered to the patient continuously.

4. The method of claim 1, wherein N,N-bis-2-mercaptoethyl isophthalamide is administered to the patient intermittently.

5. The method of claim 1, wherein N,N-bis-2-mercaptoethyl isophthalamide is administered to the patient orally, intravenously, intraarterially, intramuscularly, cutaneously, subcutaneously, transmucosally, rectally, transdermally, nasally, pulmonarily, topically, or intraperitoneally.

6. The method of claim 1, wherein N,N-bis-2-mercaptoethyl isophthalamide is administered to the patient orally, intravenously, cutaneously, subcutaneously, nasally, intramuscularly, or intraperitoneally.

7. The method of claim 1, wherein the patient is human.

8. The method of claim 1, wherein the method further comprises administering one or more additional active ingredients to the patient having MSA.

9. The method of claim 1, wherein said administering is effective to relieve symptoms of MSA.

10. The method of claim 1, wherein said administering is effective to modify progression of MSA.

* * * * *